US00PP19799P2

(12) United States Plant Patent
Hofmann

(10) Patent No.: US PP19,799 P2
(45) Date of Patent: Mar. 3, 2009

(54) **GUINEA *IMPATIENS* PLANT NAMED 'FISUPNIC ORLAV'**

(50) Latin Name: *Impatiens hawkeri*
Varietal Denomination: Fisupnic Orlav

(75) Inventor: Birgit Christa Hofmann, Bendorf (DE)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 12/077,264

(22) Filed: Mar. 18, 2008

(51) Int. Cl.
*A01H 5/00* (2006.01)

(52) U.S. Cl. ..... Plt./318.4
(58) Field of Classification Search ..... Plt./318.6
See application file for complete search history.

*Primary Examiner*—Annette H Para
(74) *Attorney, Agent, or Firm*—S. Matthew Edwards

(57) ABSTRACT

A new New Guinea *Impatiens* plant particularly distinguished by large, round, flat, lavender colored flowers with a small white eye borne well above the foliage, medium-green somewhat glossy foliage, (narrow) elliptically shaped leaves, mounded and, well-branched plant habit, and medium (mid-season) flowering response, is described.

1 Drawing Sheet

Genus and species: *Impatiens hawkeri* W. Bull.
Variety denomination: 'Fisupnic Orlav'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name, 'Fisupnic Orlav'. The new cultivar originated from a hybridization made in the year 2003 in Hillscheid, Germany. The female parent was the proprietary lilac flowered New Guinea *Impatiens* plant 'K03-2974-2' (unpatented), while the male parent was the proprietary light-lavender flowered New Guinea *Impatiens* plant 'K02-562-1' (unpatented). The seeds produced by the hybridization were sown in a greenhouse in Portugal in the fall of 2003. A single plant selection was chosen for further evaluation and for asexual propagation in March 2004 in Moncarapacho, Portugal.

The new cultivar was created in 2004 in Hillscheid, Germany and has been asexually reproduced repeatedly by vegetative cuttings and tissue culture in Moncarapacho, Portugal and Hillscheid, Germany over a three-year period. 'Fisupnic Orlav' has not been observed under all possible environmental conditions. The phenotype may vary significantly with variations in environment such as temperature, light intensity and day length, without, however, any variation in genotype. The present invention has been found to retain its distinctive characteristics through successive asexual propagations.

Plant Breeder's Rights for this cultivar were applied for in Canada on Mar. 30, 2007, and in Switzerland, on May 23, 2007. 'Fisupnic Orlav' has not been made publicly available more than one year prior to filing of this application.

SUMMARY OF THE INVENTION

The following are the most outstanding and distinguishing characteristics of this new cultivar when grown under normal horticultural practices in Hillscheid, Germany, and in Langley, British Columbia, Canada.

1. Lavender flower color with a small white eye;
2. Large, round, flat flowers, borne well above the foliage;

3. Medium-green somewhat glossy foliage, (narrow) elliptically shaped leaves;
4. Mounded and, well-branched plant habit; and
5. Medium (mid-season) flowering response.

DESCRIPTION OF PHOTOGRAPH

This New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13 weeks old, grown in a greenhouse in Hillscheid, Germany, in the late summer of 2006.

DESCRIPTION OF THE NEW CULTIVAR

The following detailed descriptions set forth the distinctive characteristics of 'Fisupnic Orlav'. The data which defines these characteristics were collected from asexual reproductions carried out in Hillscheid, Germany. The plant history was taken on 10 to 12-week old plants which were planted as rooted cuttings in 12 cm pots in late February 2007, and then grown in a greenhouse at a minimum temperature of 16° C. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—New Guinea *Impatiens* Group, *Impatiens hawkeri* W. Bull.
*Common name.*—New Guinea *Impatiens.*

Parentage:
*Female parent.*—'K03-2974-2' a proprietary lilac-flowered New-Guinea *Impatiens* plant (unpatented).

*Male parent.*—'K02-562-1' a proprietary New-Guinea *Impatiens* plant, light-lavender flowered (unpatented).

Growth:

*Growth and branching habit.*—Medium to tall in size, round, bushy, and well-branched; the growth is indeterminate, though weak after the beginning of flowering.

*Height.*—13.6 cm.

*Width.*—27.7 cm.

*Propagation.*—Terminal tips for cuttings.

*Time to produce a finished flowering plant.*—10 weeks for a 12 cm pot.

*Time to initiate and develop roots.*—18 days at 22° C.

Branches:

*Stem.*—Average number: 9.8. Length of branches: 9 cm to 12 cm. Internode length: About 3 cm to 5 cm. Diameter of branches: 0.7 cm to 1.1 cm. Stem color: Mainly RHS 144C (light green); RHS 179A or RHS 180A (reddish) at the nodes.

Leaves:

*Arrangement.*—Primarily in whorls, often 5 leaves per whorl.

*Size.*—Length: 13.7 cm. Width: 4.6 cm.

*Shape.*—Lanceolate to elliptical.

*Margin.*—Slightly serrate, ciliated.

*Apex.*—Acuminate.

*Base.*—Acute.

*Color (immature leaves).*—Upper surface: RHS 137D. Lower surface: RHS 138B.

*Color (mature leaves).*—Upper surface: Near RHS 137A. Lower surface: Near RHS 138B.

*Texture.*—Upper surface: Glabrous, smooth to slightly rippled, somewhat glossy. Lower surface: Glabrous, smooth, apart from the protruding veins.

*Venation color.*—Upper surface: Mainly RHS 145B (light green), RHS 180D (brown-pink) near base. Lower surface: RHS 182D (light pink).

*Variegation.*—None.

*Petioles.*—Length: 1.3 cm on average. Diameter: 0.3 cm to 0.4 cm. Color: Upper surface: RHS 179B (reddish). Lower surface: RHS 144C (light green), or RHS 182D (pink). Texture: Glabrous.

Flower buds:

*Shape.*—Ovoid.

*Size.*—Length: 2.0 cm to 2.2 cm. Diameter: 1.3 cm to 1.5 cm.

*Color.*—RHS N74D (lavender to purple-pink).

Inflorescence:

*Blooming habit.*—9 to 10 weeks after planting of rooted cuttings.

*Inflorescence type.*—Flowers appear solitary in the leaf axiles of the upper nodes of the stems.

*Number of flowers per node.*—5 to 7, in various stages of development.

*Flowering season.*—Indeterminate, mainly from April to October, or longer depending on light intensity and temperature.

*Lastingness of individual blooms.*—Up to about 10–12 days in a greenhouse at 18° C. in spring.

*Fragrance.*—Absent.

*Peduncle.*—Color: RHS 144B (light green) to RHS 144C (light green); may partly show weak infusion of anthocyanin, resulting in RHS 180D (grayed-red). Size: Length: 6.3 cm on average. Diameter: 0.2 cm. Texture: Glabrous, flexible.

Flowers:

*Form of corolla.*—Single-type, 5 petals.

*Shape of corolla.*—Nearly round, with the petals overlapping, almost flat.

*Corolla size.*—Length: 7.7 cm. Width: 7.7 cm. Depth: 1.0 cm.

Petals:

*Shape.*—Cordate, weakly lobed at the top.

*Apex.*—Retuse.

*Base.*—Attenuate.

*Margin.*—Entire.

*Petal size.*—Top: Length: 3.6 cm. Width: 6.1 cm to 6.3 cm. Lateral: Length: 3.4 cm to 3.6 cm. Width: 3.7 cm to 4.0 cm.

*Lower.*—Length: 3.6 cm to 3.9 cm. Width: 4.3 cm to 4.6 cm.

*Color.*—General color description: Mainly lavender-pink, and a small white eye. Upper surface of petals: Immature: N74C. Mature: RHS N78D, RHS N78C in parts. Lower surface: Immature: N74D. Mature: RHS 84B to RHS 84C. Eye: RHS 76D (very pale violet-purple) to RHS 155A (white) at base of mainly lateral and lower petals.

*Texture.*—Upper surface: Glabrous, smooth, slightly glossy. Lower surface: Glabrous, smooth.

*Aspect.*—Mature petals are flat, and horizontally directed, parallel to the foliage canopy.

Calyx:

*General.*—3 sepals visible, a large one transformed into a spur, two lateral, scale-like spurs, and the $4^{th}$ and $5^{th}$ fused, crestlike, under the banner petal.

*Spur shape.*—Downwardly curved.

*Color.*—RHS 53D (deep pink).

*Size.*—Length: 6.3 cm. Diameter: Base: 0.3 cm. Apex: 0.05 cm.

*Lateral sepals.*—Color: RHS 143B (green). Shape: Oval. Length: About 1.0 cm. Diameter: 0.6 cm wide. Margin: Entire.

Reproductive organs:

*Stamens.*—Number: 5. Stamen color (upper surface color): Mainly RHS 155A (white), with a small macule of RHS 75B. Anthers: Fused, hooded. Pollen color: RHS 8D (whitish-yellow).

*Pistils.*—Style and stigma: 5, very short, RHS 150D (pale yellow). Ovary length: 0.6 cm. Ovary color: RHS 143A (green).

Fruit and seed set: No seed set observed.

Disease and insect resistance: No particular resistance or susceptibility has been observed.

COMPARISON WITH PARENTAL AND COMMERCIAL CULTIVARS

'Fisupnic Orlav' differs from the female parent 'K03-2974-2' (unpatented) by having a lighter overall flower color, a white eye, and earlier flowering.

'Fisupnic Orlav' differs from the male parent 'K02-562-1' (unpatented), by having a somewhat deeper flower color, slightly deeper foliage color, and somewhat tighter plant habit.

'Fisupnic Orlav' differs from the commercial cultivar 'Fisco Lav' (U.S. Plant Pat. No. 17,364) by having a slightly less deep hue of flower color, lighter green foliage, stems with weaker or no anthocyanin coloration, and a taller plant habit.

'Fisupnic Orlav' differs from cultivar 'Fisimp 114' (U.S. Plant Pat. No. 13,698) by having a somewhat lighter hue of flower color, a more distinct white 'eye', and slightly less deep green foliage. Furthermore, the aspect of the leaves is slanting upward for 'Fisupnic Orlav', while the leaves of 'Fisimp 114' are mostly horizontally directed.

'Fisupnic Orlav' differs from cultivar 'BFP-865' (U.S. Plant Pat. No. 11,445) in that 'Fisupnic Orlav' has a somewhat lighter overall flower color, somewhat lighter green foliage, and less compact habit.

'Fisupnic Orlav' differs from cultivar 'Fisnics Lilav' (U.S. Plant Pat. No. 14,746) by having deeper lavender colored flowers with less distinctly lobed petals, narrower leaves, and taller plant habit.

I claim:

1. A new and distinct cultivar of New Guinea *Impatiens* plant as shown and described herein.

* * * * *

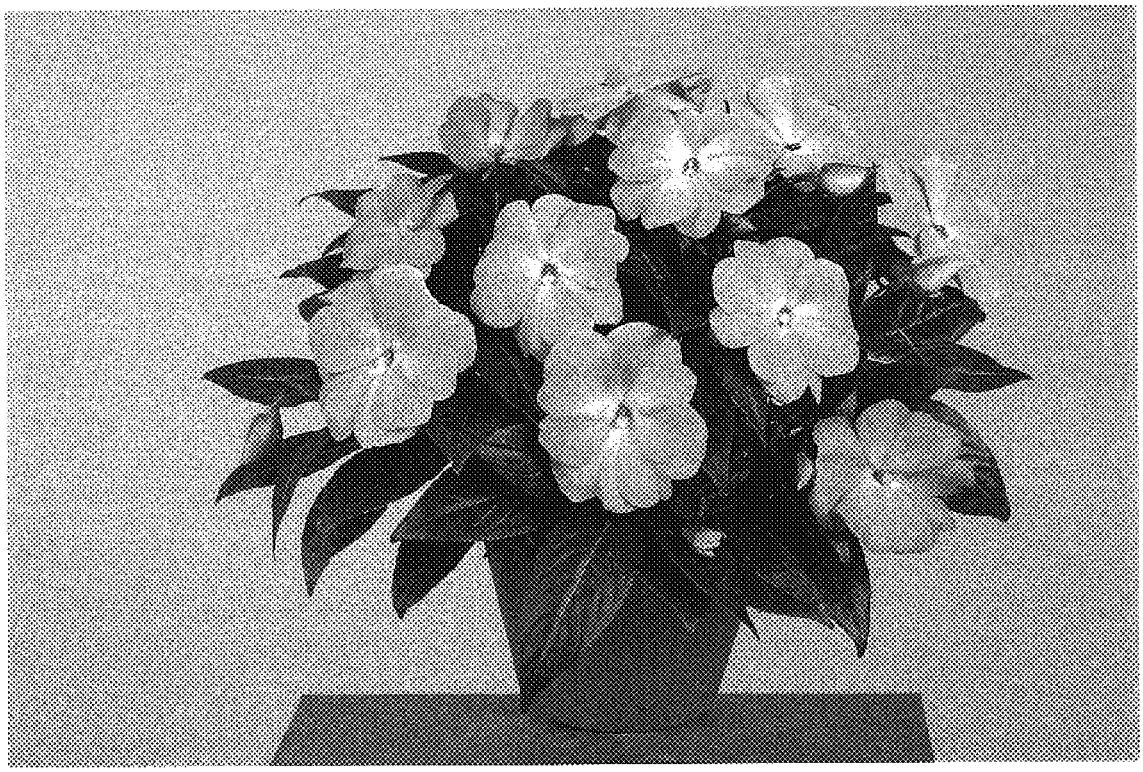

UNITED STATES PATENT AND TRADEMARK OFFICE

CERTIFICATE OF CORRECTION

PATENT NO. : PP 19,799 P2
APPLICATION NO. : 12/077264
DATED : March 3, 2009
INVENTOR(S) : Hofmann It is certified that error appears in the above-identified patent and that said Letters Patent is hereby corrected as shown below:

On page 1, in the title (54), please insert --New-- before “Guinea”

Signed and Sealed this

Twenty-eighth Day of July, 2009

John Doll

JOHN DOLL
*Acting Director of the United States Patent and Trademark Office*